United States Patent
Schneider-Fresenius et al.

(10) Patent No.: US 7,052,687 B2
(45) Date of Patent: *May 30, 2006

(54) HUMAN RECOMBINANT BETA-INTERFERON WITH IMPROVED SOLUBILITY

(75) Inventors: Christian Schneider-Fresenius, Hannover (DE); Bernd Otto, Hannover (DE); Gero Waschütza, Meinersen (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 46 days.

This patent is subject to a terminal disclaimer.

(21) Appl. No.: 10/448,667

(22) Filed: May 30, 2003

(65) Prior Publication Data

US 2004/0022763 A1 Feb. 5, 2004

Related U.S. Application Data

(63) Continuation of application No. 09/403,532, filed as application No. PCT/EP98/02238 on Apr. 16, 1998, now Pat. No. 6,572,853.

(30) Foreign Application Priority Data

Apr. 23, 1997 (DE) ................................ 197 17 864

(51) Int. Cl.
*A61K 38/21* (2006.01)
*C07K 14/00* (2006.01)
*C12P 21/04* (2006.01)

(52) U.S. Cl. .................... 424/85.6; 424/85.4; 530/351; 435/69.51

(58) Field of Classification Search ................. 530/350
See application file for complete search history.

(56) References Cited

U.S. PATENT DOCUMENTS 4,588,585 A 5/1986 Mark et al.
5,350,836 A 9/1994 Kopchick et al.

FOREIGN PATENT DOCUMENTS

EP 0 163 993 5/1985

OTHER PUBLICATIONS

Luck et al., Molecular Endocrinology 1991, vol. 5(12): pp. 1880-1886, esp. p. 1881, table 1.*
Gibson et al., J Immunol. 2001, vol. 166(6): pp. 3915-3922, esp. p. 3915.*
Shepard et al., Nature. 1981, vol. 294(5841): pp. 563-565 (esp. p. 563: Title and Table 1).*
Kruse et al. Embo J., 1993, vol. 12, No. 13, pp. 5121-5129.

* cited by examiner

*Primary Examiner*—Janet L. Andres
*Assistant Examiner*—Jegatheesan Seharaseyon
(74) *Attorney, Agent, or Firm*—Barnes & Thornburg LLP

(57) ABSTRACT

The invention relates to variants of recombinant human beta interferon and to a method for the production thereof, wherein at least one of the following amino acids Leu (5), Phe(8), Phe(15), Leu(47), Phe(50), Leu(106), Phe(111), Leu(116), Leu(120) and Phe(156) are exchanged with hydrophilic amino acid with a hydroxy group, specially serine, tyrosine or threonine, resulting in enhanced hydrophilic property of the protein surface.

19 Claims, 4 Drawing Sheets

| | | | | | | | | | | | |
|---|---|---|---|---|---|---|---|---|---|---|---|
| Met<br>1 | Ser | Tyr | Asn | Leu<br>5 | Leu | Gly | Phe | Leu | Gln<br>10 | Arg | Ser |
| Ser | Asn<br>Asn<br>25 | Phe<br>15 | Gln | Cys | Gln | Lys | Leu<br>20 | Leu | Trp | Gln | Leu |
| Gly | Arg<br>Phe | Leu | Glu | Tyr<br>30 | Cys | Leu | Lys | Asp | Arg<br>35 | Met | Asn |
| Asp | Ile<br>Gln<br>40 | Pro | Glu | Glu | Ile | Lys<br>45 | Gln | Leu | Gln | Gln | Phe<br>50 |
| Lys | Glu<br>Gln | Asp | Ala<br>55 | Ala | Leu | Thr | Ile | Tyr<br>60 | Glu | Met | Leu |
| Asn | Ile<br>Thr<br>65 | Phe | Ala | Ile | Phe<br>70 | Arg | Gln | Asp | Ser<br>75 | Ser | Ser |
| Gly | Trp<br>Asn<br>80 | Asn | Glu | Thr | Ile | Val<br>85 | Glu | Asn | Leu | Leu | Ala |
| Val<br>90 | Tyr<br>Glu | His | Gln | Ile<br>95 | Asn | His | Leu | Lys | Thr<br>100 | Val | Leu |
| Glu | Lys<br>Leu<br>105 | Leu | Glu | Lys | Glu | Asp<br>110 | Phe | Thr | Arg | Gly | Lys<br>115 |
| Met | Ser<br>Ile | Ser | Leu<br>120 | His | Leu | Lys | Arg | Tyr<br>125 | Tyr | Gly | Arg |
| Leu | His<br>Ala<br>130 | Tyr | Leu | Lys | Ala<br>135 | Lys | Glu | Tyr | Ser | His<br>140 | Cys |
| Trp | Thr<br>Tyr<br>145 | Ile | Val | Arg | Val | Glu | Ile<br>150 | Leu | Arg | Asn | Phe |
| Phe<br>155 | Ile | Asn | Arg | Leu<br>160 | Thr | Gly | Tyr | Leu | Arg<br>165 | Asn | |

(SEQ ID No. 1)

Fig. 1

Met Ser Tyr Asn Xaa Leu Gly Xaa Leu Gln Arg Ser
1           5                   10
Ser Asn Xaa Gln Cys Gln Lys Leu Leu Trp Gln Leu
    Asn
        15              20
        25
Gly Arg Leu Glu Tyr Cys Leu Lys Asp Arg Met Asn
    Phe
                30              35
Asp Ile Pro Glu Glu Ile Lys Gln Xaa Gln Gln Xaa
    Gln
        40              45              50
Lys Glu Asp Ala Ala Leu Thr Ile Tyr Glu Met Leu
    Gln
            55              60
Asn Ile Phe Ala Ile Phe Arg Gln Asp Ser Ser Ser
    Thr
65              70              75
Gly Trp Asn Glu Thr Ile Val Glu Asn Leu Leu Ala
    Asn
        80              85
        90
Val Tyr His Gln Ile Asn His Leu Lys Thr Val Leu
    Glu
                95              100
Glu Lys Xaa Glu Lys Glu Asp Xaa Thr Arg Gly Lys
    Xaa
        105             110             115
Met Ser Ser Xaa His Leu Lys Arg Tyr Tyr Gly Arg
    Ile
            120             125
Leu His Tyr Leu Lys Ala Lys Glu Tyr Ser His Cys
    Ala
130             135             140

Trp Thr Ile Val Arg Val Glu Ile Xaa Arg Asn Phe
    Tyr
        145             150
        155
Phe Ile Asn Arg Leu Thr Gly Tyr Leu Arg Asn
                160             165
(SEQ ID No. 2)

Fig. 2

Met Ser Tyr Asn Ser Leu Gly Ser Leu Gln Arg Ser
 1              5                   10
Ser Asn Ser Gln Cys Gln Lys Leu Leu Trp Gln Leu
        15                  20
Asn Gly Arg Leu Glu Tyr Cys Leu Lys Asp Arg Met
 25                  30                  35
Asn Phe Asp Ile Pro Glu Glu Ile Lys Gln Ser Gln Gln Ser
            40                  45                  50
Lys Glu Gln Asp Ala Ala Leu Thr Ile Tyr Glu Met Leu
        55                  60
Asn Ile Thr Phe Ala Ile Phe Arg Gln Asp Ser Ser Ser
 65                  70                  75
Gly Trp Asn Asn Glu Thr Ile Val Glu Asn Leu Leu Ala
            80                  85
Val Tyr Glu His Gln Ile Asn His Leu Lys Thr Val Leu
        90                  95                  100
Glu Lys Ser Ser Glu Lys Glu Asp Ser Thr Arg Gly Lys
            105                 110                 115
Met Ser Ile Ser Ser His Leu Lys Arg Tyr Tyr Gly Arg
            120                 125
Leu His Ala Tyr Leu Lys Ala Lys Glu Tyr Ser His Cys
 130                 135                 140

Trp Thr Tyr Ile Val Arg Val Glu Ile Leu Arg Asn Phe
        145                 150
 155
Ser Ile Asn Arg Leu Thr Gly Tyr Leu Arg Asn
            160                 165
(SEQ ID No. 3)

Fig. 3

| | | |
|---|---|---|
| L5 | 5'-CTCCCTTGGATTCCTACAAAGAAGC-3' | 25 (SEQ ID No. 4) |
| F8 | 5'-CTTGCTTGGATCCCTACAAAGAAGC-3' | 25 (SEQ ID No. 5) |
| F15/C17 | 5'-AGCAGCAATTCTCAGTCCCAGAAGCTCC-3' | 28 (SEQ ID No. 6) |
| C17 | 5'-AGCAGCAATTTTCAGTCCCAGAAGCTCC-3' | 28 (SEQ ID No. 7) |
| L47 | 5'-TTAAGCAGTCCCAGCAGTTCCAGAAGG-3' | 27 (SEQ ID No. 8) |
| F50 | 5'-TTAAGCAGCTGCAGCAGTCCCAGAAGG-3' | 27 (SEQ ID No. 9) |
| L106 | 5'-GAAGAAAAATCCGAGAAGAAGATTTCACC-3' | 30 (SEQ ID No.10) |
| F111 | 5'-GAAGAAAAACTGGAGAAAGAAGATTCCACC-3' | 30 (SEQ ID No.11) |
| L116 | 5'-AAAATCCATGAGCAGTCTGCACCTG-3' | 25 (SEQ ID No.12) |
| L120 | 5'-AAAACTCATGAGCAGTTCCCACCTG-3' | 25 (SEQ ID No.13) |
| F156 | 5'-ACTTTTACTCCATTAACAGACCTACAGG-3' | 28 (SEQ ID No.14) |
| L5/F3Rev | 5'-TTGTAGCTCATATGTAAGTATTTCC-3' | 25 (SEQ ID No.15) |
| F15/C17Rev | 5'-TCTTTGTAGGAATCCAAGCAAGTTGTAGC-3' | 29 (SEQ ID No.16) |
| L47/F50Rev | 5'-TCTCCTCAGGGATGTCAAAGTTCATCC-3' | 27 (SEQ ID No.17) |
| L106/F111Rev | 5'-CAGGACTGTCTTCAGATGGTTTATCTG-3' | 27 (SEQ ID No.18) |
| L116/L120Rev | 5'-CCCCTGGTGAAATCTTCTTTCTC-3' | 23 (SEQ ID No.19) |
| F156Rev | 5'-TTCTTAGGATTTCCACTCTGACTATGG-3' | 27 (SEQ ID No.20) |
| L5-C17Rev | 5'-TCTTTGTAGGGATCCAAGGGAGTTGTAGC-3' | 29 (SEQ ID No.21) |
| L106-L130Rev | 5'-CCCCTGGTGGAATCTTCTTTCTCGGA-3' | 26 (SEQ ID No.22) |

Fig. 4

HUMAN RECOMBINANT BETA-INTERFERON WITH IMPROVED SOLUBILITY

CROSS-REFERENCE TO RELATED APPLICATIONS

This application a continuation application of U.S. Ser. No. 09/403,532, filed Feb. 22, 2000 now U.S. Pat. No. 6,572,853. U.S. Ser. No. 09/403,532 is the U.S. national phase of PCT/EP98/02238, filed Apr. 16, 1998. PCT/EP98/02238 claims the benefit of Federal Republic of Germany patent application serial number 197 17 864.2, filed Apr. 23, 1997. The disclosures of all of these prior applications are expressly incorporated by reference herein.

The invention pertains to variants of human recombinant beta-interferon with improved solubility.

Beta-interferon is a regulatory protein which leads to activation of genes by binding receptors. As a result, antiviral, antiproliferative and further biological activities are mediated in the cell.

The inteferons, as is also the case with the interleukins, belong to the class of cytokines and are subdivided into different classes:

Type I interferon (alpha, beta, omega, tau) and Type II (gamma)

Human beta-interferon is a protein with a molecular weight of 22 kDa and 166 amino acid residues. It is formed primarily in fibroblasts during attack by a virus and possesses antiviral, antiproliferative and further biological activities. The amino acid sequence of human beta-interferon was first published by Taniguchi et al. (1980), Gene Ed. 10, pages 11 through 15, and is illustrated in FIG. 1.

Beta-interferon, which is produced from bacteria cells or mammalian cells by genetic engineering, is being used successfully in the treatment of multiple sclerosis, a previously incurable disease in a large group of patients. However, the very high hydrophobicity of the protein, which causes very poor Solubility of recombinant human beta-interferon, proves to be problematical for the production and processing of recombinant human beta-interferon.

The problem for the present invention is to make available variants of recombinant human beta-interferon whose solubility is improved in polar media, such as e.g. aqueous liquids. In addition, an objective of this invention is to indicate processes for manufacturing and possibilities for using variants of recombinant human beta-interferon with higher solubility in polar media such as aqueous liquids.

This problem is solved by the recombinant human beta-interferon in accordance with claim 1, its use in accordance with claim 5 and its manufacture in accordance with claim 6 or 7.

In accordance with claim 1, at least one of the following ten hydrophobic amino acids in known human beta-interferon is exchanged for a hydrophilic amino acid: Leu invention pertains to individual mutations as well as to all the possible combinations of these individual amino acid exchanges.

The designated amino acids are essentially located on the surface of human beta-interferon and they take up a relatively large proportion of the surface there. The exchange of these amino acids therefore leads to more than a proportionately large improvement in the hydrophilic character of the surface of recombinant human beta-interferon and it therefore increases the solubility of this protein in polar media, such as e.g. aqueous liquids. As a result of its increased hydrophilicity, the recombinant human beta-interferon in accordance with the invention is considerably simpler to handle in production as well as during its processing to give an active substance.

The production of the variants of recombinant human beta-interferon in accordance with the invention takes place in a generally known, conventional way with the help of microorganisms, e.g. in an *Escherichia coli* culture which has been provided with the gene for one of the proteins in accordance with the invention. The production of these microorganisms, which have been changed by means of genetic engineering, also takes place in a generally known way with the help of classical genetic engineering mutagenesis procedures for the exchange of the corresponding amino acids for hydrophilic amino acids and their synthesis will therefore be dispensed with at this juncture.

The proteins in accordance with the invention find use for the manufacture of medicinal drugs, e.g. for combatting multiple sclerosis, as well as fine chemicals for in vitro experiments or for measurements of interferon levels. The improved hydrophilicity of these proteins thereby simplifies their manufacture, transportation, storage and application in the form of a medicinal drug or fine chemical.

Advantageous further developments of the proteins in accordance with the invention are given in the dependent claims.

Exchange for the amino acids serine, tyrosine and threonine is especially advantageous and, with one hydroxy group each, these are especially hydrophilic.

As a result of its small size, serine is especially suitable for exchange since especially slight steric changes in the protein are associated with it.

The amino acid sequence of native recombinant human beta-interferon, in which the above-mentioned ten amino acids are electively exchanged for serine, is illustrated in FIG. 2. These exchangeable amino acids are represented by Xaa. If these amino acids are exchanged, then the hydrophilicity of the surface of recombinant human beta-interferon is very much improved whereas only slight impairment arises in terms of the functionality and the efficacy of human recombinant beta-interferon.

An especially advantageous further development is illustrated in FIG. 3 in which all of the above-mentioned ten amino acids have been exchanged here for serine so that an especially marked increase in the hydrophilicity of the surface of recombinant human beta-interferon results.

An example of a variant of human recombinant beta-interferon in accordance with the invention is given in the following sections:

FIG. 1 shows native human recombinant beta-interferon;

FIG. 2 shows the variants of recombinant human beta-interferon in accordance with the invention;

FIG. 3 shows a recombinant human beta-interferon [variant] in accordance with the invention; and FIG. 4 shows primers for the mutagenesis for the manufacture of beta-interferon in accordance with the invention.

As already described above, FIG. 1 describes native human recombinant beta-interferon in the form in which it can already be manufactured currently with the help of known molecular biological and bio-technical possibilities.

The sequence of native human recombinant beta-interferon is illustrated in FIG. 2 in which Xaa designates those amino acids which can be exchanged for an amino acid with at least one hydroxy group (advantageously serine, tyrosine and/or threonine) and hence result in a recombinant human beta-interferon [variant] in accordance with the invention which possesses increased surface hydrophilicity.

By way of example, all ten individual variants of beta-interferon have been manufactured in which Leu (5), Phe (8), Phe (15), Leu (47), Phe (50), Leu (106), Phe (111), Leu (116), Leu (120) or Phe (156) were exchanged for serine, whereby, in particular, the variants with exchange of the amino acids Leu (5), Phe (8), Leu (47), Phe (50), Leu (106), Phe (111), Leu (116) and Leu (120) relative to native beta-interferon, and also these variants of the Cys-17-Ser variant of human beta-interferon, excel by virtue of comparable biological activity.

FIG. 3 shows an example of a human recombinant beta-interferon [variant] in which the following amino acids have been exchanged for serine:

Leu (5), Phe (8), Phe (15), Leu (47), Phe (50), Leu (106), Phe (111), Leu (116), Leu (120) and Phe (156). In the case of this variant of recombinant human beta-interferon, especially high hydrophilicity of the surface of the protein results and, hence, especially good solubility in aqueous solutions.

For example, the multiple variant with amino acid exchanges at positions 47, 50, 106, 111, 116 and 120 also shows activity which corresponds to the beta-interferon starting protein, with a Cys17Ser exchange, which was used in this example.

The manufacture of organisms with a gene, which has been changed in accordance with the invention, for human recombinant beta-interferon takes place by means of classical mutagenesis procedures.

Mutagenesis takes place by means of a PCR (polymerase chain reaction). The mutations are introduced via synthetic oligonucleotides. Plasmid DNA with the beta-IFN gene [translator: beta-INF gene?] serves as the template. The entire plasmid was replicated with the PCR method which was used here. The selection of the PCR fragments takes place by means of restriction digestion of the entire PCR mixture with the enzyme DpnI. This enzyme recognizes only methylated interfaces. Since fragments, which are produced in vitro by means of PCR, are unmethylated, only the template DNA is degraded by DpnI. After DpnI digestion, in the event of success, a fragment with the length of the linearized template remains behind and this carries the mutations. The PCR fragments, that are produced, are cloned and sequenced.

| PCR mixture (100 ml): | template DNA | 10 mg |
| --- | --- | --- |
| | primers | 100 pmol each |
| | nucleotide mix | 200 mM per dNTP |
| | MgSO$_4$ | 2–6 mM |
| | DNA polymerase | 2.5 units |
| PCR protocol | Duration | Temperature |
| step 1. | 4 min | 95 C. |
| step 2. | +enzyme | |
| step 3. | 45 sec | 95 C. |
| step 4. | 1 min | 55 C. |
| step 5. | 10 min | 68 C. |
| | | goto [sic] 3. (11×) |
| step 6. | 10 min | 68 C. |
| step 7. | | 4 C. |

The PCR was carried out in a Thermocycler PTC-200 (MJ Research company).

Two primers are necessary for each PCR, namely a "forward" primer and a "reverse" primer. The two primers follow one another directly but, in each case, they bind to different strands with the opposite orientation.

FIG. 4 illustrates primers which were used for the mutagenesis in order that the amino acid(s), that are designated on the left, be exchanged for serine in the gene product, i.e. the beta-interferon in accordance with the invention.

The last two primers alone contain "reverse" primer mutations. A PCR with these primers additionally introduces mutations without the previously inserted mutations 5/8 or 106/111 being relinquished. If the wild type is taken as a template, then four mutations can be introduced at the same time via the "reverse" primers (5–17 or, as the case may be, 106–120).

SEQUENCE LISTING

<160> NUMBER OF SEQ ID NOS: 26

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
              100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa = Leu, Ser, Tyr, or Thr
<220> FEATURE:
<221> NAME/KEY: MISC_FEATURE
<222> LOCATION: (8)..(8)
<223> OTHER INFORMATION: Xaa = Phe, Ser, Tyr, or Thr
<220> FEATURE:
<221> NAME/KEY: MISC_FEATURE
<222> LOCATION: (15)..(15)
<223> OTHER INFORMATION: Xaa = Phe, Ser, Tyr, or Thr
<220> FEATURE:
<221> NAME/KEY: MISC_FEATURE
<222> LOCATION: (47)..(47)
<223> OTHER INFORMATION: Xaa = Leu, Ser, Tyr, or Thr
<220> FEATURE:
<221> NAME/KEY: MISC_FEATURE
<222> LOCATION: (50)..(50)
<223> OTHER INFORMATION: Xaa = Phe, Ser, Tyr, or Thr
<220> FEATURE:
<221> NAME/KEY: MISC_FEATURE
<222> LOCATION: (106)..(106)
<223> OTHER INFORMATION: Xaa = Leu, Ser, Tyr, or Thr
<220> FEATURE:
<221> NAME/KEY: MISC_FEATURE
<222> LOCATION: (111)..(111)
<223> OTHER INFORMATION: Xaa = Phe, Ser, Tyr, or Thr
<220> FEATURE:
<221> NAME/KEY: MISC_FEATURE
<222> LOCATION: (116)..(116)
<223> OTHER INFORMATION: Xaa = Leu, Ser, Tyr, or Thr
<220> FEATURE:
<221> NAME/KEY: MISC_FEATURE
<222> LOCATION: (120)..(120)
<223> OTHER INFORMATION: Xaa = Leu, Ser, Tyr, or Thr
<220> FEATURE:
<221> NAME/KEY: MISC_FEATURE
<222> LOCATION: (151)..(151)
<223> OTHER INFORMATION: Xaa = Leu, Ser, Tyr, or Thr

<400> SEQUENCE: 2

Met Ser Tyr Asn Xaa Leu Gly Xaa Leu Gln Arg Ser Ser Asn Xaa Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Xaa Gln
        35                  40                  45

Gln Xaa Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

-continued

```
Glu Thr Ile Val Glu Asn Leu Leu Ala Asn Val Tyr His Gln Ile Asn
                85                  90                  95

His Leu Lys Thr Val Leu Glu Glu Lys Xaa Glu Lys Glu Asp Xaa Thr
            100                 105                 110

Arg Gly Lys Xaa Met Ser Ser Xaa His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Xaa Arg Asn Phe Tyr Phe Ile Asn Arg Leu
145                 150                 155                 160

Thr Gly Tyr Leu Arg Asn
                165

<210> SEQ ID NO 3
<211> LENGTH: 166
<212> TYPE: PRT
<213> ORGANISM: Homo sapiens

<400> SEQUENCE: 3

Met Ser Tyr Asn Ser Leu Gly Ser Leu Gln Arg Ser Ser Asn Ser Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Ser Gln
        35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Ser Ile Asn Arg Leu
145                 150                 155                 160

Thr Gly Tyr Leu Arg Asn
                165

<210> SEQ ID NO 4
<211> LENGTH: 25
<212> TYPE: DNA
<213> ORGANISM: Artificial sequence
<220> FEATURE:
<223> OTHER INFORMATION: Description of Artificial Sequence:  Primer for
      Homo sapiens beta
      -interferon, wherein nucleotides are altered to substitute a seri
      ne for another amino acid
<220> FEATURE:
<221> NAME/KEY: mutation
<222> LOCATION: (3)..(4)
<223> OTHER INFORMATION: Leu to Ser mutation

<400> SEQUENCE: 4
ctcccttgga ttcctacaaa gaagc                                             25
```

-continued

```
<210> SEQ ID NO 5
<211> LENGTH: 25
<212> TYPE: DNA
<213> ORGANISM: artificial sequence
<220> FEATURE:
<223> OTHER INFORMATION: Description of Artificial Sequence:  Primer for
      Homo sapiens beta
      -interferon, wherein nucleotides are altered to substitute a seri
      ne for another amino acid
<220> FEATURE:
<221> NAME/KEY: mutation
<222> LOCATION: (12)..(12)
<223> OTHER INFORMATION: Phe to Ser mutation

<400> SEQUENCE: 5
cttgcttgga tccctacaaa gaagc                                            25

<210> SEQ ID NO 6
<211> LENGTH: 28
<212> TYPE: DNA
<213> ORGANISM: artificial sequence
<220> FEATURE:
<223> OTHER INFORMATION: Description of Artificial Sequence:  Primer for
      Homo sapiens beta
      -interferon, wherein nucleotides are altered to substitute a seri
      ne for another amino acid
<220> FEATURE:
<221> NAME/KEY: mutation
<222> LOCATION: (11)..(11)
<223> OTHER INFORMATION: Phe to Ser mutation
<220> FEATURE:
<221> NAME/KEY: mutation
<222> LOCATION: (17)..(18)
<223> OTHER INFORMATION: Cys to Ser mutation

<400> SEQUENCE: 6
agcagcaatt ctcagtccca gaagctcc                                         28

<210> SEQ ID NO 7
<211> LENGTH: 28
<212> TYPE: DNA
<213> ORGANISM: Artificial sequence
<220> FEATURE:
<223> OTHER INFORMATION: Description of Artificial Sequence:  Primer for
      Homo sapiens beta
      -interferon, wherein nucleotides are altered to substitute a seri
      ne for another amino acid
<220> FEATURE:
<221> NAME/KEY: mutation
<222> LOCATION: (17)..(18)
<223> OTHER INFORMATION: Cys to Ser mutation

<400> SEQUENCE: 7
agcagcaatt ttcagtccca gaagctcc                                         28

<210> SEQ ID NO 8
<211> LENGTH: 27
<212> TYPE: DNA
<213> ORGANISM: Artificial sequence
<220> FEATURE:
<223> OTHER INFORMATION: Description of Artificial Sequence:  Primer for
      Homo sapiens beta
      -interferon, wherein nucleotides are altered to substitute a seri
      ne for another amino acid
<220> FEATURE:
<221> NAME/KEY: mutation
<222> LOCATION: (9)..(11)
<223> OTHER INFORMATION: Leu to Ser mutation

<400> SEQUENCE: 8
ttaagcagtc ccagcagttc cagaagg                                          27
```

<210> SEQ ID NO 9
<211> LENGTH: 27
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (19)..(19)
<223> OTHER INFORMATION: Phe to Ser mutation

<400> SEQUENCE: 9
ttaagcagct gcagcagtcc cagaagg                                       27

<210> SEQ ID NO 10
<211> LENGTH: 30
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (10)..(12)
<223> OTHER INFORMATION: Leu to Ser mutation

<400> SEQUENCE: 10
gaagaaaaat ccgagaaaga agatttcacc                                    30

<210> SEQ ID NO 11
<211> LENGTH: 30
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (26)..(26)
<223> OTHER INFORMATION: Phe to Ser mutation

<400> SEQUENCE: 11
gaagaaaaac tggagaaaga agattccacc                                    30

<210> SEQ ID NO 12
<211> LENGTH: 25
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (5)..(6)
<223> OTHER INFORMATION: Leu to Ser mutation

<400> SEQUENCE: 12
aaaatccatg agcagtctgc acctg                                         25

<210> SEQ ID NO 13
<211> LENGTH: 25

```
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (17)..(19)
<223> OTHER INFORMATION: Leu to Ser mutation

<400> SEQUENCE: 13
aaaactcatg agcagttccc acctg                                          25

<210> SEQ ID NO 14
<211> LENGTH: 28
<212> TYPE: DNA
<213> ORGANISM: Artificial sequence
<220> FEATURE:
<223> OTHER INFORMATION: Description of Artificial Sequence: Primer for
      Homo sapiens beta
      -interferon, wherein nucleotides are altered to substitute a seri
      ne for another amino acid
<220> FEATURE:
<221> NAME/KEY: mutation
<222> LOCATION: (10)..(10)
<223> OTHER INFORMATION: Phe to Ser mutation

<400> SEQUENCE: 14
acttttactc cattaacaga cctacagg                                       28

<210> SEQ ID NO 15
<211> LENGTH: 25
<212> TYPE: DNA
<213> ORGANISM: Artificial sequence
<220> FEATURE:
<223> OTHER INFORMATION: Description of Artificial Sequence: Reverse
      primer for Homo sapi
      ens beta-interferon, wherein nucleotides in the forward primer ar
      e altered to substitute a serine for another amino acid

<400> SEQUENCE: 15
ttgtagctca tatgtaagta tttcc                                          25

<210> SEQ ID NO 16
<211> LENGTH: 29
<212> TYPE: DNA
<213> ORGANISM: Artificial sequence
<220> FEATURE:
<223> OTHER INFORMATION: Description of Artificial Sequence: Reverse
      primer for Homo sapi
      ens beta-interferon, wherein nucleotides in the forward primer ar
      e altered to substitute a serine for another amino acid

<400> SEQUENCE: 16
tctttgtagg aatccaagca agttgtagc                                      29

<210> SEQ ID NO 17
<211> LENGTH: 27
<212> TYPE: DNA
<213> ORGANISM: Artificial sequence
<220> FEATURE:
<223> OTHER INFORMATION: Description of Artificial Sequence: Reverse
      primer for Homo sapi
      ens beta-interferon, wherein nucleotides in the forward primer ar
      e altered to substitute a serine for another amino acid

<400> SEQUENCE: 17
tctcctcagg gatgtcaaag ttcatcc                                        27
```

<210> SEQ ID NO 18
<211> LENGTH: 27
<212> TYPE: DNA
<213> ORGANISM: Artificial sequence
<220> FEATURE:
<223> OTHER INFORMATION: Description of Artificial Sequence: Reverse
    primer for Homo sapi
    ens beta-interferon, wherein nucleotides in the forward primer ar
    e altered to substitute a serine for another amino acid

<400> SEQUENCE: 18
caggactgtc ttcagatggt ttatctg                               27

<210> SEQ ID NO 19
<211> LENGTH: 23
<212> TYPE: DNA
<213> ORGANISM: Artificial sequence
<220> FEATURE:
<223> OTHER INFORMATION: Description of Artificial Sequence: Reverse
    primer for Homo sapi
    ens beta-interferon, wherein nucleotides in the forward primer ar
    e altered to substitute a serine for another amino acid

<400> SEQUENCE: 19
cccctggtga aatcttcttt ctc 23

<210> SEQ ID NO 20
<211> LENGTH: 27
<212> TYPE: DNA
<213> ORGANISM: Artificial sequence
<220> FEATURE:
<223> OTHER INFORMATION: Description of Artificial Sequence: Reverse
primer for Homo sapi
ens beta-interferon, wherein nucleotides in the forward primer ar
e altered to substitute a serine for another amino acid

<400> SEQUENCE: 20
ttcttaggat ttccactctg actatgg 27

<210> SEQ ID NO 21
<211> LENGTH: 29
<212> TYPE: DNA
<213> ORGANISM: Artificial sequence
<220> FEATURE:
<223> OTHER INFORMATION: Description of Artificial Sequence: Reverse
primer for Homo sapi
ens beta-interferon, wherein nucleotides are altered to substitut
e a serine for another amino acid
<220> FEATURE:
<221> NAME/KEY: mutation
<222> LOCATION: (11)..(11)
<223> OTHER INFORMATION: Leu to Ser mutation
<220> FEATURE:
<221> NAME/KEY: mutation
<222> LOCATION: (19)..(20)
<223> OTHER INFORMATION: Cys to Ser mutation

<400> SEQUENCE: 21
tctttgtagg gatccaaggg agttgtagc 29

<210> SEQ ID NO 22
<211> LENGTH: 26
<212> TYPE: DNA
<213> ORGANISM: Artificial sequence
<220> FEATURE:
<223> OTHER INFORMATION: Description of Artificial Sequence: Reverse
primer for Homo sapi
ens beta-interferon, wherein nucleotides are altered to substitut
e a serine for another amino acid <220> FEATURE:
<221> NAME/KEY: mutation
<222> LOCATION: (10)..(10)
<223> OTHER INFORMATION: Leu to Ser mutation
<220> FEATURE:
<221> NAME/KEY: mutation
<222> LOCATION: (24)..(26)
<223> OTHER INFORMATION: Leu to Ser mutation

<400> SEQUENCE: 22
cccctggtgg aatcttcttt ctcgga                                          26

<210> SEQ ID NO 23
<211> LENGTH: 166
<212> TYPE: PRT
<213> ORGANISM: Homo sapiens

<400> SEQUENCE: 23

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Ser Gln
            35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110

Arg Gly Lys Ser Met Ser Ser His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 24
<211> LENGTH: 166
<212> TYPE: PRT
<213> ORGANISM: Homo sapiens

<400> SEQUENCE: 24

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Ser Gln
            35                  40                  45

Gln Ser Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Ser Glu Lys Glu Asp Ser Thr
            100                 105                 110
Arg Gly Lys Ser Met Ser Ser Ser His Leu Lys Arg Tyr Tyr Gly Arg
        115                 120                 125
Ile Leu His Tyr Leu Lys Ala Lys Glu Tyr Ser His Cys Ala Trp Thr
    130                 135                 140
Ile Val Arg Val Glu Ile Leu Arg Asn Phe Tyr Phe Ile Asn Arg Leu
145                 150                 155                 160
Thr Gly Tyr Leu Arg Asn
                165

<210> SEQ ID NO 25
<211> LENGTH: 166
<212> TYPE: PRT
<213> ORGANISM: Homo sapiens

<400> SEQUENCE: 25

Met Ser Tyr Asn Ser Leu Gly Ser Leu Gln Arg Ser Ser Asn Phe Gln
1               5                   10                  15
Ser Gln Lys Leu Leu Trp Gln Leu Asn Gly Arg Leu Glu Tyr Cys Leu
            20                  25                  30
Lys Asp Arg Met Asn Phe Asp Ile Pro Glu Glu Ile Lys Gln Ser Gln
        35                  40                  45
Gln Ser Gln Lys Glu Asp Ala Ala Leu Thr Ile Tyr Glu Met Leu Gln
    50                  55                  60
Asn Ile Phe Ala Ile Phe Arg Gln Asp Ser Ser Ser Thr Gly Trp Asn
65                  70                  75                  80
Glu Thr Ile Val Glu Asn Leu Leu Ala Asn Val Tyr His Gln Ile Asn
                85                  90                  95
His Leu Lys Thr Val Leu Glu Glu Lys Ser Glu Lys Glu Asp Ser Thr
            100                 105                 110
Arg Gly Lys Ser Met Ser Ser Ser His Leu Lys Arg Tyr Tyr Gly Arg
        115                 120                 125
Ile Leu His Tyr Leu Lys Ala Lys Glu Tyr Ser His Cys Ala Trp Thr
    130                 135                 140
Ile Val Arg Val Glu Ile Leu Arg Asn Phe Tyr Phe Ile Asn Arg Leu
145                 150                 155                 160
Thr Gly Tyr Leu Arg Asn
                165

<210> SEQ ID NO 26
<211> LENGTH: 166
<212> TYPE: PRT
<213> ORGANISM: Homo sapiens

<400> SEQUENCE: 26

Met Ser Tyr Asn Ser Leu Gly Ser Leu Gln Arg Ser Ser Asn Phe Gln
1               5                   10                  15
Cys Gln Lys Leu Leu Trp Gln Leu Asn Gly Arg Leu Glu Tyr Cys Leu
            20                  25                  30
Lys Asp Arg Met Asn Phe Asp Ile Pro Glu Glu Ile Lys Gln Ser Gln
        35                  40                  45
Gln Ser Gln Lys Glu Asp Ala Ala Leu Thr Ile Tyr Glu Met Leu Gln
    50                  55                  60
Asn Ile Phe Ala Ile Phe Arg Gln Asp Ser Ser Ser Thr Gly Trp Asn
65                  70                  75                  80

```
Glu Thr Ile Val Glu Asn Leu Leu Ala Asn Val Tyr His Gln Ile Asn
            85                  90                  95
His Leu Lys Thr Val Leu Glu Glu Lys Ser Glu Lys Glu Asp Ser Thr
            100                 105                 110
Arg Gly Lys Ser Met Ser Ser Ser His Leu Lys Arg Tyr Tyr Gly Arg
            115                 120                 125
Ile Leu His Tyr Leu Lys Ala Lys Glu Tyr Ser His Cys Ala Trp Thr
            130                 135                 140
Ile Val Arg Val Glu Ile Leu Arg Asn Phe Tyr Phe Ile Asn Arg Leu
145                 150                 155                 160
Thr Gly Tyr Leu Arg Asn
                165
```

What is claimed is:

1. Human recombinant beta-interferon, wherein at least one of the amino acids Leu (5), Phe (8), Phe (15), Leu (47), Phe (50), Leu (106), Phe (111), Leu (116), Leu (120), and Phe (156) has been exchanged for an amino acid with at least one hydroxyl group.

2. Beta-interferon in accordance with claim 1, wherein the amino acid with the hydroxyl group is selected from the group consisting of serine, tyrosine, and threonine.

3. Beta-interferon in accordance with claim 1 or 2, wherein the beta-interferon contains the amino acid sequence of SEQ ID NO: 2, wherein SEQ ID NO: 2 contains the following amino acid sequence:

```
Met Ser Tyr Asn Xaa Leu Gly Xaa Leu Gln Arg Ser
1               5                   10
Ser Asn Xaa Gln Cys Gln Lys Leu Leu Trp Gln Leu
            15                  20
Asn Gly Arg Leu Glu Tyr Cys Leu Lys Asp Arg Met
25                  30                  35
Asn Phe Asp Ile Pro Glu Glu Ile Lys Gln Xaa Gln
            40                  45
Gln Xaa Gln Lys Glu Asp Ala Ala Leu Thr Ile Tyr
    50              55                      60
Glu Met Leu Gln Asn Ile Phe Ala Ile Phe Arg Gln
            65                  70
Asp Ser Ser Ser Thr Gly Trp Asn Glu Thr Ile Val
        75                  80
Glu Asn Leu Leu Ala Asn Val Tyr His Gln Ile Asn
85                  90                  95
His Leu Lys Thr Val Leu Glu Glu Lys Xaa Glu Lys
            100                 105
Glu Asp Xaa Thr Arg Gly Lys Xaa Met Ser Ser Xaa
    110                 115                 120
His Leu Lys Arg Tyr Tyr Gly Arg Ile Leu His Tyr
            125                 130
Leu Lys Ala Lys Glu Tyr Ser His Cys Ala Trp Thr
            135                 140
Ile Val Arg Val Glu Ile Xaa Arg Asn Phe Tyr Xaa
145                 150                 155
Ile Asn Arg Leu Thr Gly Tyr Leu Arg Asn
                160                 165
``` wherein at least one or more of the amino acids Xaa(5), Xaa(8), Xaa (15), Xaa(47), Xaa(50), Xaa(106), Xaa (111), Xaa(116), Xaa(120), Xaa(156) is serine, tyrosine or threonine and the following applies to the other amino acids Xaa(5) is Leu, Xaa(8) is Phe, Xaa(15) is Phe, Xaa(47) is Leu, Xaa(50) is Phe, Xaa(106) is Leu, Xaa(111) is Phe, Xaa(116) is Leu, Xaa(120) is Leu, Xaa(156) is Phe.

4. Beta-interferon in accordance with claim 1, 2, or 3, wherein the beta-interferon contains the amino acid sequence of SEQ ID NO: 3, wherein SEQ ID NO: 3 contains the following amino acid sequence:

```
Met Ser Tyr Asn Ser Leu Gly Ser Leu Gln Arg Ser
1               5                   10
Ser Asn Ser Gln Cys Gln Lys Leu Leu Trp Gln Leu
            15                  20
Asn Gly Arg Leu Glu Tyr Cys Leu Lys Asp Arg Met
25                  30                  35
Asn Phe Asp Ile Pro Glu Glu Ile Lys Gln Ser Gln
            40                  45
Gln Ser Gln Lys Glu Asp Ala Ala Leu Thr Ile Tyr
    50              55                      60
Glu Met Leu Gln Asn Ile Phe Ala Ile Phe Arg Gln
            65                  70
Asp Ser Ser Ser Thr Gly Trp Asn Glu Thr Ile Val
        75                  80
Glu Asn Leu Leu Ala Asn Val Tyr His Gln Ile Asn
85                  90                  95
His Leu Lys Thr Val Leu Glu Glu Lys Ser Glu Lys
            100                 105
```

```
                                        -continued

Glu Asp Ser Thr Arg Gly Lys Ser Met Ser Ser Ser
    110                 115                 120

His Leu Lys Arg Tyr Tyr Gly Arg Ile Leu His Tyr
            125                 130

Leu Lys Ala Lys Glu Tyr Ser His Cys Ala Trp Thr
        135                 140

Ile Val Arg Val Glu Ile Leu Arg Asn Phe Tyr Ser
145                 150                 155

Ile Asn Arg Leu Thr Gly Tyr Leu Arg Asn.
            160                 165
```

5. A human recombinant beta-interferon wherein each of the amino acids Leu (47), Phe (50), Leu (106), Phe (111), Leu (116), and Leu (120) has been exchanged for an amino acid with at least one hydroxyl group.

6. A human recombinant beta-interferon wherein each of the amino acids Cys (17), Leu (47), Phe (50), Leu (106), Phe (111), Leu (116), and Leu (120) has been exchanged for an amino acid with at least one hydroxyl group.

7. A human recombinant beta-interferon wherein each of the amino acids Leu (5), Phe (8) Phe (15), Leu (47), Phe (50), Leu (106), Phe (111), Leu (116), and Leu (120) has been exchanged for an amino acid with at least one hydroxyl group.

8. Human recombinant beta-interferon wherein Leu(5) has been exchanged for an amino acid with at least one hydroxyl group.

9. Human recombinant beta-interferon wherein Phe(8) has been exchanged for an amino acid with at least one hydroxyl group.

10. Human recombinant beta-interferon wherein Phe(15) has been exchanged for an amino acid with at least one hydroxyl group.

11. Human recombinant beta-interferon wherein Leu(47) has been exchanged for an amino acid with at least one hydroxyl group.

12. Human recombinant beta-interferon wherein Phe(50) has been exchanged for an amino acid with at least one hydroxyl group.

13. Human recombinant beta-interferon wherein Leu (106) has been exchanged for an amino acid with at least one hydroxyl group.

14. Human recombinant beta-interferon wherein Phe(111) has been exchanged for an amino acid with at least one hydroxyl group.

15. Human recombinant beta-interferon wherein Leu (116) has been exchanged for an amino acid with at least one hydroxyl group.

16. Human recombinant beta-interferon wherein Leu (120) has been exchanged for an amino acid with at least one hydroxyl group.

17. Human recombinant beta-interferon wherein Phe (156) has been exchanged for an amino acid with at least one hydroxyl group.

18. Human recombinant beta-interferon in accordance with claim 1 or any one of claims 5–17 wherein the amino acid with at least one hydroxyl group is selected from the group consisting of serine, tyrosine, and threonine.

19. Human recombinant beta-interferon in accordance with claim 1 or any of claims 5–17 wherein the amino acid with at least one hydroxyl group is serine.

* * * * *